United States Patent [19]

Kabbe et al.

[11] B 3,997,533
[45] Dec. 14, 1976

[54] PROCESS FOR THE PREPARATION OF 7-ACYLAMINO-DESACETOXYCEPHALOSPORANIC DERIVATIVES

[75] Inventors: Hans-Joachim Kabbe, Leverkusen; Uwe Petersen, Cologne, both of Germany

[73] Assignee: Bayer Aktiengesellschaft, Germany

[22] Filed: Feb. 14, 1974

[21] Appl. No.: 442,810

[44] Published under the second Trial Voluntary Protest Program on February 24, 1976 as document No. B 442,810.

[30] Foreign Application Priority Data

Feb. 26, 1973  Germany .......................... 2309599

[52] U.S. Cl. ........................ 260/243 C; 424/246; 260/239.1
[51] Int. Cl.$^2$ ...................... C07D 501/10

[58] Field of Search ................................ 260/243 C

[56] References Cited

UNITED STATES PATENTS

| 3,725,397 | 4/1973 | Graham et al. | 260/243 C |
| 3,725,399 | 4/1973 | Ellerton et al. | 260/243 C |
| 3,781,283 | 12/1973 | Bormann et al. | 260/243 C |
| 3,799,924 | 3/1974 | Jackson et al. | 260/243 C |
| 3,852,281 | 12/1974 | Verweij | 260/243 C |
| 3,853,861 | 12/1974 | Garbrecht | 260/243 C |

*Primary Examiner*—Nicholas S. Rizzo

[57]  ABSTRACT

7-Acylaminodesacetoxycephalosporanic acid derivatives are produced by heating a penicillin ester S-oxide to a temperature between 60° C and 150° C in the presence of a heavy metal salt.

14 Claims, No Drawings

PROCESS FOR THE PREPARATION OF 7-ACYLAMINO-DESACETOXYCEPHALOSPORANIC DERIVATIVES

The present invention relates to a novel process for the preparation of known 7-acylaminodesacetoxycephalosporanic acid derivatives.

It is known according to U.S. Pat. No. 3,275,626 that S-oxides of 6-acylaminopenicillanic acid esters can, at elevated temperatures in the presence of acid catalysts, be converted into 7-acylaminodesacetoxycephalosporanic acid esters. According to this process, however, mixtures are formed which have such a low content of the desired cephalosporanic acid derivatives that commerical use of the process is practically impossible.

An improvement in that process was described in German Offenlegungsschrift No. 2,006,689. This process comprises the additional use of amides as solvents and the rearrangement results in about a 70 percent yield when sulphonic acids are used as acid catalysts. This process, however, has the disadvantage that in order to obtain a 70 percent yield the reaction solutions must be heated for several hours, for example, 12 hours, in a boiling mixture of benzene and dimethylacetamide, or for 12 hours in dimethylacetamide at 100°C.

The process of the present invention overcomes the disadvantages of the prior art processes and enables 7-acylaminodesacetoxycephalosporanic acid derivatives to be produced in good yield in an economic process.

More particularly, the process of the present invention comprises the production of 7-acylaminodesacetoxycephalosporanic acid derivatives of the formula

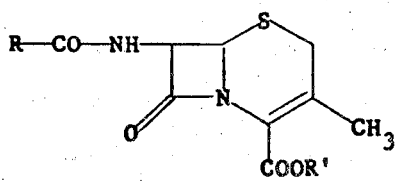

(I)

wherein

R is benzyl, phenoxymethyl, tert.-butoxy, 2-thenyl, cyanomethyl, alkyl of 1 to 6 carbon atoms, benzyl substituted in the ring by at least one substituent selected from the group consisting of hydroxy, alkoxy of 1 to 4 carbon atoms, alkyl-mercapto of 1 to 4 carbon atoms and halogen, benzyl substituted in the methylene group by at least one substituent selected from the group consisting of alkyl of 1 to 4 carbon atoms, amino, azido, acylamino of 1 to 6 carbon atoms, alkoxycarbonyl of 1 to 6 carbon atoms in the alkoxy moiety and

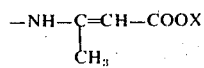

wherein

X is alkyl of 1 to 4 carbon atoms;

R' is p-nitrobenzyl, p-methoxybenzyl, β,β, β-trichloroethyl, diphenylmethyl, 9-fluorenyl, tert.-butyl, trityl, phenacyl, p-chlorophenacyl, p-bromophenacyl, p-nitrophenacyl, p-phenylphenacyl or cyanomethyl; which comprises heating a penicillin ester S-oxide of the formula

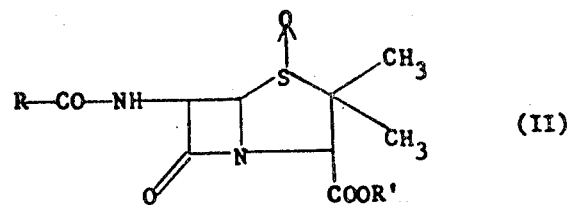

(II)

wherein

R and R' are as above defined, to a temperature between 60° C and 150° C in the presence of a heavy metal salt catalyst of the formula

Me(R''SO₃)ₙ     (III)

wherein

Me is copper, silver, gold, zinc, cadmium, mercury, thallium, tin, lead, iron, cobalt or nickel; R'' is alkyl of 1 to 4 carbon atoms, fluoroalkyl of 1 to 4 carbon atoms or phenyl or naphthyl unsubstituted or substituted by at least one substituent selected from the group consisting of methyl and halogen; and n is 1, 2 or 3, depending on the valency of the metal Me.

R and R' are moieties which on the one hand are stable under the reaction conditions but on the other hand can be removed under other conditions without the cephalosporanic acid ring system being attacked.

Preferred metals Me include copper, tin, silver, mercury and thallium, particularly copper, tin, silver and thallium.

The course taken by the reaction is surprising because of the use of salt for the rearrangement is not taught by U.S. Pat. No. 3,275,626 and German Offenlegungsschrift No. 2,006,689.

In particular, it could not be foreseen that rearrangement with the use of the heavy metal salt catalysts could be achieved in a far shorter reaction time period than the prior art suggests. Thus, the process according to the present invention represents a significant advance in the art.

While specific salts have already been mentioned as rearrangements catalysts, e.g., phosphoric acid salts of weak bases (see German Offenlegungsschrifts No. 2,011,351 and 2,011,376) and phosphonium salts (see German Offenlegungsschrift No. 2,064,107), nevertheless the conversion by sulphonates of heavy metals is surprising because both by the phosphate of these heavy metals and by the alkali metal salts of sulphonic acids, isomeric compounds and not the desired cephalosporin derivatives are formed as are shown by comparative Examples A and B set forth below.

If penicillin-V-sulphoxide p-nitrobenzyl ester is used as the starting compound, the reaction course can be represented by the following equation:

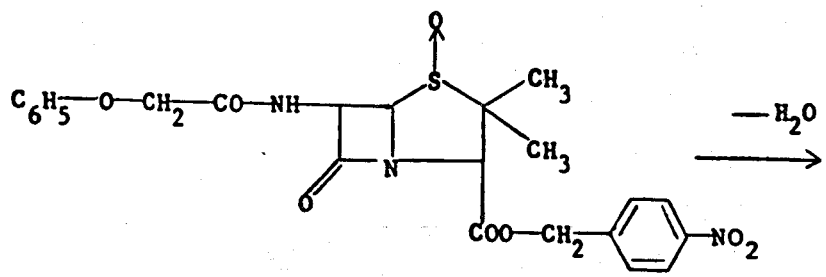

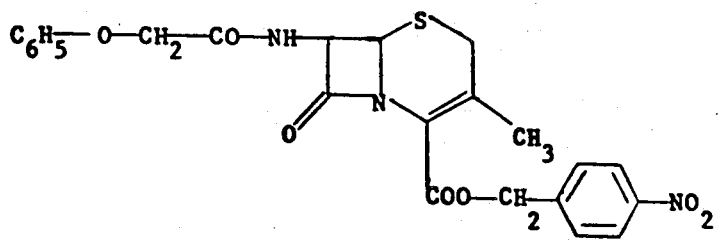

The preparation of the penicillin sulphoxide esters used as starting materials is known from the literature; it can be achieved, for example, by oxidation of penicillin salts to give 6-acylaminopenicillansulphoxide acids and subsequent esterification [*J. Am. Chem. Soc.*, 91, 1401 (1969)] or by oxidation of 6-acylaminopenicillanic acid esters with suitable oxidizing agents, such as sodium metaperiodate, hydrogen peroxide or peracids.

The reaction is expediently carried out in the presence of a diluent; as such diluents, those are preferably used which boil in the stated temperature range, especially hydrocarbons such as benzene, toluene, xylene, cyclohexane and methylcyclohexane; halogenated hydrocarbons such as chloroform, dichloroethane and chlorobenzene; nitrohydrocarbons such as nitromethane, nitroethane and nitrobenzene; open-chain and cyclic ethers such as dibutyl ether, tetrahydrofuran, dioxan and ethyleneglycol dimethyl ether; ketones such as methyl isopropyl ketone, methyl isobutyl ketone and cyclohexanone; esters such as butyl acetate or isoamyl acetate; nitriles such as acetonitrile or propionitrile; amides such as dimethyl formamide, dimethyl acetamide, N-methylpyrrolidone and hexamethylphosphoric acid tris-amide; tetra-alkyl ureas such as tetramethyl urea, 1-(1-pyrrolidylcarbonyl)-pyrrolidine or N,N-dimethyl-N',N'-tetramethylene urea; sulphoxides such as dimethyl sulphoxide; and sulphones such as tetramethylene sulphone as well as mixtures of these solvents; preferably mixtures of a less polar diluent (e.g., benzene, toluene, methylcyclohexane) with a more strongly polar one (e.g., amides, sulphoxides) are used.

The heavy metal salts of formula III are generally used in an amount of 1 to 20, preferably 3 to 10, mol percent, based on the S-oxide used, but the reaction can also be carried out successfully in the presence of larger amounts of metal salt.

The reaction is carried out at temperatures between 60° C and 150° C, preferably between 80° C and 130° C, the reaction duration and product purity being greater at lower temperatures. The reaction time is generally 10 minutes to 5 hours.

The reaction may be carried out at atmospheric pressure but also at increased pressure. Most expediently, the reaction conditions are so selected that the reaction can proceed under reflux at atmospheric pressure.

In the process according to the present invention, the processes customary in organic chemistry can be used for the removal of the water forming in the reaction by either distilling the water off azeotropically with the solvent and recycling the latter or passing the returning solvent portion over dehydrating agents such as anhydrous sodium sulphate or molecular sieves or by adding to the mixture substances which react readily with water such as ketals, acetals, ortho-esters or aminals.

For working up, the solution is preferably concentrated almost to dryness and the end products and by-products are separated either by recrystallization, by chromatography or by the addition of solvents in which only the by-products are soluble. It is also possible to add water to the reaction mixture and extract with a water-immiscible solvent such as toluene or chloroform the cephalosporin derivative which has been formed. The organic portion is concentrated and the end product remaining behind is purified; for example, by recrystallization or by dissolving out of by-products.

The cephalosporin derivatives produced by the process of the present invention can be spectroscopically and chromatographically distinguished both from the starting materials and from by-products produced during the course of the reaction.

The following nonlimitative examples more particularly illustrate the process of the present invention:

EXAMPLE 1

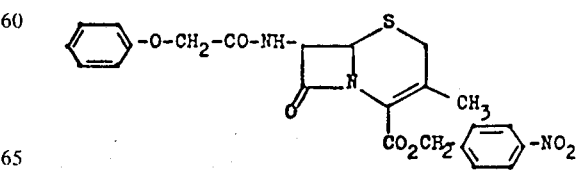

10 g penicillin-V-sulphoxide p-nitrobenzyl ester, 120 ml toluene, 60 ml dimethyl acetamide and 0.4 g tin(II)

methanesulphonate are heated to reflux temperature for 60 minutes; the toluene vapor is recycled via a water separator. After cooling, the mixture is diluted with 200 -l toluene, and extracted once with 100 ml of water; the organic portion is dried over sodium sulphate and concentrated. The residue is stirred together with 100 ml of a 1:1 mixture of isopropanol and ether. 7.1 g (73%) of 7-phenoxyacetamido-3-methyl-Δ-3-cephem-4-carboxylic acid p-nitrobenzyl ester of the melting point 189°–191°C are obtained, which was identified with authentic material by thin-layer chromatography, elementary analysis, and infrared, nuclear magnetic resonance and mass spectrography.

EXAMPLE 2

The same procedure is followed as in Example 1, but only 0.1 g tin(II) methanesulphonate is used, and the reactants were heated to reflux temperature for 2 hours. 6.8 g (70%) of the same compound as in Example 1 are obtained.

EXAMPLE 3

10 g penicillin-V-sulphoxide p-nitrobenzyl ester, 120 ml toluene, 30 ml dimethyl acetamide and 0.4 g silver methanesulphonate are heated to reflux temperature for 1½ hours and worked up as in Example 1. 7.65 g (79%) of 7-phenoxyacetamido-3-methyl-Δ3-cephem-4-carboxylic acid p-nitrobenzyl ester of the melting point 186°–188°C are formed.

EXAMPLE 4

The same procedure is followed as in Example 3, but 0.4 g copper(II) methanesulphonate are used as catalyst. 7.6 g (78%) of the crystalline 7-phenoxyacetamido-3-methyl-Δ3-cephem-4-carboxylic acid p-nitrobenzyl ester are formed, which according to nuclear resonance spectrum no longer contain any starting material.

EXAMPLE 5

2.5 g penicillin-V-sulphoxide p-nitrobenzyl ester, 30 ml toluene, 20 ml dimethyl sulphoxide and 0.1 g silver methanesulphonate are heated to reflux temperature for 1 hour. Working up as in the preceding Examples yields 1.05 g (44%) of 7-phenoxyacetamido-3-methyl-Δ3-cephem-4-carboxylic acid p-nitrobenzyl ester.

EXAMPLE 6

5 g penicillin-V-sulphoxide p-nitrobenzyl ester, 30 ml toluene, 20 ml dimethyl acetamide and 0.3 g thallium-(III) methane sulphonate are heated to the boil on a water separator for 1 hour. Working up as usual yields 3 g (62%) of 7-phenoxyacetamido-3-methyl-Δ3-cephem-4-carboxylic acid p-nitrobenzyl ester, m.p. 184°–187°C.

EXAMPLE 7

The same procedure is followed as in Example 6, but with 0.2 g mercury(II) methanesulphonate, and 2.9 g (60%) of 7-phenoxyacetamido-3-methyl-Δ3-cephem-4-carboxylic acid p-nitrobenzyl ester, m.p. 182-185°C, are obtained.

EXAMPLE 8

The same procedure is followed as in Example 3 but, as solvent, a mixture of 80 ml toluene, 80 ml dimethyl acetamide and 40 ml methylcyclohexane is used and 7.4 g (76%) of 7-phenoxyacetamido-3-methyl-Δ3-cephem-4-carboxylic acid p-nitrobenzyl ester of m.p. 189°–191°C are obtained.

EXAMPLE 9

5 g penicillin-V-sulphoxide p-nitrobenzyl ester, 25 ml toluene, 25 ml methylcyclohexane, 25 ml dimethyl acetamide and 0.1 g silver trifluoromethanesulphonate are heated to the boil on a water separator for 1 hour. After working up in the usual way, 2.6 g (54%) of 7-phenoxyacetamido-3-methyl-Δ3-cephem-4-carboxylic acid p-nitrobenzyl ester of m.p. 183°–186°C are obtained.

EXAMPLE 10

The same procedure is followed as in Example 6 but using as catalyst 0.2 g silver p-toluenesulphonate, and 2.9 g (60%) of 7-phenoxyacetamido-3-methyl-Δ3-cephem-4-carboxylic acid p-nitrobenzyl ester of m.p. 185°–188°C are obtained.

EXAMPLE 11

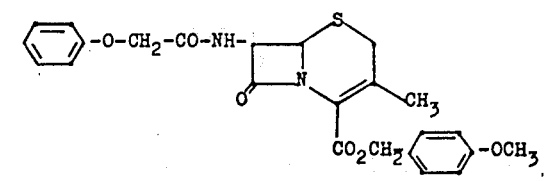

2.4 g penicillin-V-sulphoxide p-methoxybenzyl ester are heated for 1 hour under reflux with 0.1 g tin(II) methanesulphonate in 15 ml toluene and 7.5 ml dimethyl acetamide. After cooling, 50 ml toluene and 50 ml water are added, and the toluene phase is isolated and dried with sodium sulphate. After evaporation of the solvent, 5 ml methanol are added to the oil remaining behind and the crystalline product which precipitates is filtered off with suction after it has stood for a time. 1.2 g (52%) of 7-phenoxyacetamido-3-methyl-Δ3-cephem-4-carboxylic acid p-methoxybenzyl ester of melting point 153°–156°C are isolated, the structure of which is confirmed by nuclear resonance, infrared and mass spectrum.

EXAMPLE 12

2.4 g penicillin-V-sulphoxide p-methoxybenzyl ester are catalytically rearranged with 0.1 g silver methanesulphonate as described in Example 11, and yield 1.0 g (43%) 7-phenoxyacetamido-3-methyl-Δ3-cephem-4-carboxylic acid p-methoxybenzyl ester of melting point 153°–156°C.

EXAMPLE 13

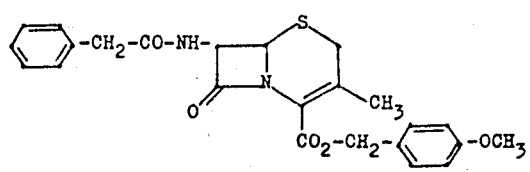

9.4 g benzylpenicillin sulphoxide p-methoxybenzyl ester in 120 ml toluene and 60 ml dimethyl acetamide with 0.4 g silver methanesulphonate are heated under reflux for 1 hour on a water separator. After cooling, and dilution with 100 ml of water followed by extraction with 100 ml toluene, the organic phase is dried with sodium sulphate and the solvent evaporated at 60°C in a water-pump vacuum. 10 ml methanol are added to the residue and, after standing for a longer period, there are isolated 4.8 g (53%) of a product of melting point 165°–167°C (from methanol) which, according to elementary analysis and nuclear resonance and infrared spectra is 7-phenylacetamido-3-methyl-Δ3-cephem-4-carboxylic acid p-methoxybenzyl ester.

EXAMPLE 14

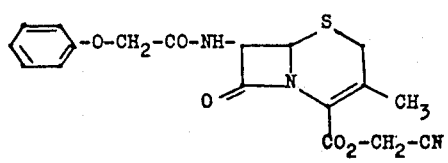

2 g penicillin-V-sulphoxide cyanomethyl ester are heated under reflux for 1 hour with 0.1 g tin(II) methanesulphonate in 15 ml toluene, 10 ml dimethyl acetamide and 10 ml methylcyclohexane. After cooling, 50 ml toluene and 50 ml of water are added to the reaction mixture and the organic phase is separated and dried with sodium sulphate. After evaporation of the toluene in a vacuum, 5 ml methanol are added to the oily residue. After some time, 7-phenoxyacetamido-3-methyl-Δ3-cephem-4-carboxylic acid cyanomethyl ester of the melting point 143°–145°C (decomposition) crystallizes out in a yield of 1.0 g (52%). Nuclear resonance, infrared and mass spectra confirm the structure.

EXAMPLE 15

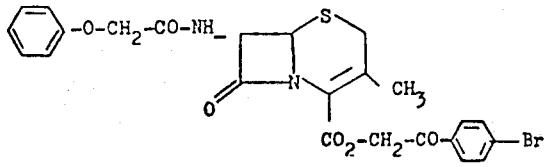

2.65 g penicillin-V-sulphoxide p-bromophenacyl ester are heated under reflux for 1 hour in 15 ml toluene and 7.5 ml dimethyl acetamide with 0.1 g silver methanesulphonate and, after cooling, shaken with 50 ml of water and 50 ml toluene. The organic phase is dried with sodium sulphate, concentrated, and 5 ml methanol are added to the residue. The crystalline 7-phenoxyacetamido-3-methyl-Δ3-cephem-4-carboxylic acid p-bromophenacyl ester is filtered off with suction, washed with methanol and dried. Yield: 1.55 g (63%) of the melting point 178°–181°C (decomposition). Infrared and nuclear resonance spectrum confirm the structure.

Penicillin-V-sulphoxide-p-bromophenacyl ester is prepared in the following manner:

A solution of 6.5 g penicillin-V-sulphoxide acid, 2.6 ml triethylamine and 4.85 g p-bromophenacyl bromide is stirred in 55 ml acetone for 4 hours at room temperature and 100 ml of water are then added. The precipitate is filtered off with suction and recrystallized from ethanol. Yield: 8.4 g (84%) penicillin-V-sulphoxide p-bromophenacyl ester of the melting point 169°–170°(decomposition).

EXAMPLE 16

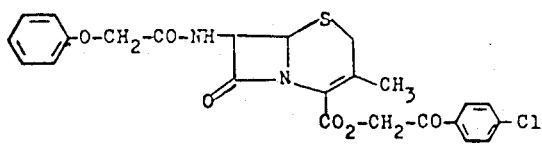

2.43 g penicillin-V-sulphoxide p-chlorophenacyl ester are reacted and worked up under the conditions of Example 15. Yield: 1.9 g (81%) 7-phenoxyacetamido-3-methyl-Δ3-cephem-4-carboxylic acid p-chlorophenacyl ester of the melting point 185°–186°C (from acetonitrile). Infrared and nuclear resonance spectra confirm the structure. Penicillin-V-sulphoxide p-chlorophenacyl ester of the melting point 156°–157° (decomposition) is prepared as described above for the preparation of penicillin-V-sulphoxide p-bromophenacyl ester from penicillin-V-sulphoxide acid and p-chlorophenacyl bromide in a yield of 83%.

EXAMPLE 17

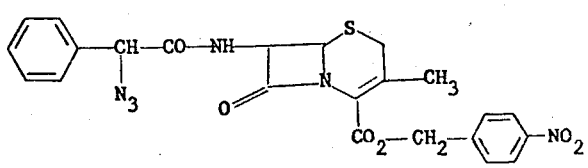

2.6 g Azidocillin-sulphoxide-p-nitrobenzyl ester are reacted and worked up under the conditions of Example 15. Yield: 0,7g (28%)7-(α-azido-phenylacetamido)-3-methyl-Δ³cephem-4-carboxylic acid-p-nitrobenzyl-ester of the melting point 184°–186°C (decomposition) from Acetonitril/Methanol. Infrared and nuclear resonance spectra confirm the structure.

Process for the production of Azidocillin-sulphoxide-p-nitrobenzyl-ester: 19 g of the sodium salt of Azidocillin are suspended in 50 ml dimethylformamide and 50 ml tetrahydrofuran. To the mixture 11 g of p-nitrobenzylbromide are added at a temperature of C°C.

The mixture is stirred for 4 hours, poured into an ice cold potassium carbonate solution. The solution is extracted with methylenechloride. The organic layer is separated, washed with water and dried with sodium sulphate. Evaporation of the solvent results in 22 g of an oil which (according to thin layer-chromatography) is azidocillin-p-nitrobenzyl ester. To the oil which is solved in 80 ml acetic acid 6,4 g of a 30% hydrogen peroxide solution are added dropwise. After stirring over night the precipitated crystals are isolated and washed with ethanol. Yield: 9.5 g Azidocillin-sulphoxide-p-nitrobenzyl ester with a melting point of 167°–168°C (decomposition).

COMPARATIVE EXAMPLE A 5 g penicillin-V-sulphoxide p-nitrobenzyl ester, 40 ml toluene and 30 ml dimethyl acetamide are heated to reflux temperature for 1 hour with lithium trifluoromethanesulphonate.

a. With 0.2 g salt, non-separable mixtures are obtained.

b. with 1.6 g salt, 1.4 g of a product (the structure of which was not elucidated) isomeric with 7-phenoxyacetamido-3-methyl-Δ3-cephem-4-carboxylic acid p-nitrobenzyl ester are formed.

COMPARATIVE EXAMPLE B

The same procedure is followed as in Example 6, but with 0.2 g silver phosphate (Ag₃PO₄) as catalyst. An oily reaction product is obtained which, according to thin-layer chromatogram, contains no or only traces of 7-phenoxyacetamido-3-methyl-Δ3-cephem-4-carboxylic acid p-nitrobenzyl ester as well as at least seven further components.

PREPARATION OF THE CATALYSTS

The sulphonates of general formula III can be prepared by dissolving the appropriate heavy metal hydroxides or carbonates in aqueous or pure sulphonic acid. In the first case, the heavy metal component is used in excess so that an approximately neutral pH value (between 5 and 7) can be established; the hydroxide excess is filtered off and the filtrate concentrated to dryness. If concentrated sulphonic acid is used, it is employed in excess, and the acid excess is removed by drying over potassium hydroxide in a high vacuum at elevated temperature.

EXAMPLE 18

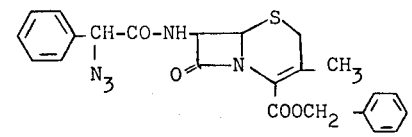

39 g Azidocillin-sulphoxide-benzylester (which is prepared according to the process for the preparation of the starting material of Example 17 and has a melting point of 155°–157°C (decomposition) are dissolved in 250 ml toluene and 150 ml dimethylacetamide and, after addition of 1,5 g tin (II)-methanesulphonate, the mixture is heated to reflux for 90 minutes the vapors being recycled via a water separator. Usual work up yields 21 g (57%) of 7-(α-azido-phenylacetamido)3-methyl-Δ³-cephem-4-carboxylic acid benzylester of the melting point 125°–127°C.

EXAMPLE 19

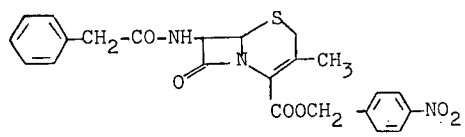

A mixture of 150 g penicillin-G-sulphoxide-p-nitrobenzylester, 1500 ml toluene, 600 ml dimethylacetamide and 6 g tin (II)-methanesulphonate are treated as in Example 18 to yield 112 g (78%) 7-phenylacetamido 3-methyl-Δ³-cephem-4-carboxylic acid-p-nitro-benzylester of the melting point 225°–227°C (after recrystallisation from acetonitrile).

What is claimed:

1. In the process for the preparation of a 7-acylamido-3-methylceph-3-em-4-carboxylate by heating the corresponding 6-acylamidopenicillanate sulfoxide at temperatures of from 60° to 150°C in an organic solvent with removal of the water formed, the improvement which comprises conducting the heating in the presence of from 1 to 20 mol percent, based on the sulfoxide present, of a heavy metal sulfonate of the formula:

$$Me(R''SO_3)_n$$

in which

Me is a cation having a valence of 1 to 3 and selected from the group consisting of the copper, silver, gold, zinc, cadmium, mercury thallium, tin, lead, iron, cobalt and nickel cations;

R'' is alkyl of 1 to 4 carbon atoms, fluoroalkyl of 1 to 4 carbon atoms, phenyl, naphthyl or phenyl or naphthyl substituted by at least one substituent selected from the group consisting of methyl and halo; and $n$ has a value of 1 to 3 and corresponds to the valence of Me.

2. The process according to claim 1 wherein Me is an anion of copper, tin, silver, mercury or thallium.

3. The process according to claim 1 wherein 3 to 10 mol percent of the heavy metal sulfonates are present.

4. The process according to claim 1 wherein the temperatures are from 80°C to 130°C.

5. The process according to claim 1 wherein the heating is conducted from about 10 minutes to about 5 hours.

6. The process according to claim 1 wherein the solvent comprises two organic solvents of differing polarities.

7. The process according to claim 1 wherein 6-acylamidopenicillanate sulfoxide is a p-nitrobenzyl ester.

8. The process according to claim 1 wherein
Me is the tin (II), silver, copper (II), thallium (III) or mercury (II) anion; and
R'' is methyl, trifluoromethyl or methylphenyl.

9. The process according to claim 1 wherein said heavy metal sulfonate is selected from the group consisting of tin (II) methanesulfonate, silver methanesulfonate, copper (II) methanesulfonate, thallium (III) methanesulfonate, mercury (II) methanesulfonate and silver p-toluenesulfonate.

10. The process according to claim 9 wherein said 6-acylamidopenicillanate sulfoxide is the p-nitrobenzyl, p-methoxy-benzyl, cyanomethyl, p-bromophenacyl or p-chlorophenacyl ester of benzylpenicillin sulfoxide, α-azidobenzylpenicillin sulfoxide or phenoxymethylpenicillin sulfoxide.

11. The process according to claim 10 wherein said sulfoxide is an ester of benzylpenicillin sulfoxide.

12. The process according to claim 11 wherein said ester is the p-nitrobenzyl ester of benzylpenicillin sulfoxide.

13. The process according to claim 10 wherein said sulfoxide is an ester of phenoxymethylpenicillin sulfoxide.

14. The process according to claim 13 wherein said ester is the p-nitrobenzyl ester of phenoxymethylpenicillin sulfoxide.

* * * * *